US007962348B2

(12) United States Patent
Dew et al.

(10) Patent No.: US 7,962,348 B2
(45) Date of Patent: Jun. 14, 2011

(54) APPARATUS, METHOD AND SOFTWARE FOR DEVELOPING ELECTRONIC DOCUMENTATION OF IMAGING MODALITIES, OTHER RADIOLOGICAL FINDINGS AND PHYSICAL EXAMINATIONS

(76) Inventors: Douglas K. Dew, Palm Coast, FL (US); Steven J. Halpern, Oviedo, FL (US); Frank J. Thomas, Lake Mary, FL (US); Charles E. Michaels, Jr., Lutz, FL (US); Clement C. Darrow, II, Bel Air, MD (US); Clement C. Darrow, III, legal representative, Bel Air, MD (US)

( * ) Notice: Subject to any disclaimer, the term of this patent is extended or adjusted under 35 U.S.C. 154(b) by 328 days.

(21) Appl. No.: 12/032,619

(22) Filed: Feb. 15, 2008

(65) Prior Publication Data
US 2008/0242953 A1 Oct. 2, 2008

Related U.S. Application Data

(60) Provisional application No. 60/890,189, filed on Feb. 15, 2007.

(51) Int. Cl.
G06Q 10/00 (2006.01)
G06Q 50/00 (2006.01)
(52) U.S. Cl. .................... 705/2; 705/3; 600/300
(58) Field of Classification Search ............ 705/2–3; 600/300
See application file for complete search history.

(56) References Cited

U.S. PATENT DOCUMENTS

| | | | |
|---|---|---|---|
| 5,146,439 A | 9/1992 | Jachmann | |
| 5,823,948 A | 10/1998 | Ross | |
| 6,047,259 A | 4/2000 | Campbell | |
| 6,684,188 B1 | 1/2004 | Mitchell | |
| 6,988,088 B1 | 1/2006 | Mukkulainen | |
| 7,461,079 B2 * | 12/2008 | Walker et al. | 707/102 |
| 2001/0041992 A1 | 11/2001 | Lewis | |
| 2002/0091687 A1 | 7/2002 | Eglington | |
| 2003/0130873 A1 | 7/2003 | Nevin | |
| 2003/0200119 A1 * | 10/2003 | Lewis et al. | 705/2 |
| 2004/0260666 A1 | 12/2004 | Pestotnik | |
| 2005/0015276 A1 | 1/2005 | Sullivan | |
| 2005/0131738 A1 * | 6/2005 | Morris | 705/2 |

* cited by examiner

*Primary Examiner* — Luke Gilligan
(74) *Attorney, Agent, or Firm* — John L. DeAngelis; Beusse Wolter Sanks Mora & Maire, P.A.

(57) ABSTRACT

A system for guiding a user's physical examination of a patient and for generating a transcript. The system comprises: a screen requesting patient identification information, wherein the patient identification information excludes a patient name and further requesting patient medical history information; a screen requesting vital signs information; a screen requesting selection of an anatomical region of the patient for examination, wherein the user selects an anatomical region responsive to the request; a screen providing a plurality of possible observed symptoms related to the selected anatomical region, wherein the user selects one or more of the possible observed symptoms; a screen presenting possible findings that may be observed during the physical examination, wherein the user selects one or more of the possible findings based on the physical examination and a screen displaying a patient transcript responsive to information entered into the previous screens.

26 Claims, 20 Drawing Sheets

FIG. 1

Automated MD - User Login

*Automated MD*
Patents Pending

User Login

Close Window

Log Out

Please enter Username and Password for access.

Username: —12
Password: —13

—15

Verify Login

The material provided in these Guidelines are designed to create Electronic Medical Records. Automated MD does not directly or indirectly practice medicine or dispense medical services. Automated MD assumes no liability for data contained or not contained in these Guidelines.

| Overview | References |
| Sponsors | Index |
| Subscribe | Support |
| Review Transcripts —17 | |

FIG. 2

Automated MD - Type of Visit

*Automated MD*
Patents Pending

Close Window
Log Out

Patient Information
Type of Visit

Patient ID: _30_

Confirm Patient ID: _32_ — _56_

Date of Birth: _34_ — _58_

Chief Complaint: _36_

Implant Data: _38_ — _42_

Type of Appointment: _40_
- Initial Appointment - New Patient
- Initial Appointment - Established Patient
- Follow-up Appointment - Established Patient
- IME (Independent Medical Examination)
- Second Opinion
- Consultation

Type of Injury:
- New injury
- No obvious injury
- Recurrent injury
- Auto injury
- Work related injury

Symptoms Duration: _44_
- Acute symptoms of less than two weeks
- Acute symptoms of greater than two weeks
- Chronic symptoms

Symptoms Progress: _46_
- Symptoms improved
- Symptoms worsening
- Symptoms unchanged Comments: _48_
No Comment

_54_    _50_

_52_ Review Transcripts    Continue — _29_

| Automated MD - Medial View, Standing - Dr Name | | |
|---|---|---|
| Automated MD Patents Pending | Exam Finalization 56 | Close Window |
| | Foot Exam (Right) 58 | Log Out |

| 304 Enter additional image data for Foot Exam |
|---|
| Enter additional Anatomy data 302 |

To add time stamped signature and finalize this transcript, enter password for Steven Halpern and click the Electronic Signature button.

Once the transcript is finalized, it can no longer be updated or changed.

Final Comments:
No Comment

Username: Steven Halpern
Password: [  ]                           308

Electronic Signature

Transcript

```
<br>
<b><u>Fracture Evaluation</u></b><br>
This is an injury of the forefoot, specifically the first distal phalanx bone Proximal Lateral<br>
<br>
<b>Displacement: </b> Severe.<br>
<br>
<b>Fracture Healing1: </b> Mild callus.<br>
<br>
<b><u>Arthritis: </u></b><br>
Arthritis of the ankle joint (tibiotalar joint) - moderate<br>
Arthritis of the Midfoot (tarsomeetatarsal joint) - mild<br>
Arthritis of the First MTP joint - severe<br>
Arthritis of the forefoot - joint fused<br>
<br>
<b>Special Considerations:</b><br><br>
Possible presence of open fracture<br>
Presence of free air plantar aspect of feet<br>
<br>
<b>ICD-9 Codes: </b>
<br>
<b><u>PATIENT EDUCATION</u></b>
According to the American Academy of Orthopedic Surgeon's "Essentials of Musculeskeletal Care," 3rd Edition, 2005<br>
<b>FRACTURES OF THE PHALANXES: pp. 639-640</b><br>
<br>
Phalangeal fracture, commonly known as a broken toe, usually involves the proximal phalanx, and is caused by direct trauma. The fifth, or little toe, is the most commonly affected. <br>
<br>
<b>DIFFERENTIAL DIAGNOSIS: </b><BR>
1. Freiberg infraction (osteonecrosis of the metatarsal head seen on radiographs) <br>
```

76
78
74         158         52

| Start Over (Image Exam) | Start Over (Physical Exam) |
| 54 Start Over (Type of Visit) | New Patient |
| Review Transcripts | Abort Exam |

Copyright © 2006-2008
Automated Clinical Guidelines, LLC.      Last Update: Thu Feb 28 18:00:00 2008      156

Ankle - Arthritis Evaluation & Special Considerations - Microsoft Internet Explorer Home Page — 504　Automated MD　506 — Close Window　← 466

Arthritis Evaluation & Special Considerations

Arthritis vs. No Arthritis Present | Special Considerations

☐ No noticeable difference

☐ Ankle arthroplasty

☐ Presence of free air in ankle joint
☐ Presence of possible open fracture

☐ Joint effusion of the ankle
☐ Joint calcification of the ankle

☐ Osteopenia of the ankle bones
☐ Osteomalacia of the ankle bones
☐ Osteopetrosis of the ankle bones ☐ Possible osteomyelitis - talus
☐ Possible osteomyelitis - fibula
☐ Possible osteomyelitis - tibia ☐ Possible tumor talus
☐ Possible tumor - fibula
☐ Possible tumor - tibia ☐ Possible foreign body - talus
☐ Possible foreign body - fibula
☐ Possible foreign body - tibia ☐ Partial bone loss - talus
☐ Possible bone loss - fibula
☐ Possible bone loss - tibia ☐ Bone cyst - talus
☐ Bone cyst - fibula
☐ Bone cyst - tibia ☐ Hardware present - talus
☐ Hardware present - fibula
☐ Hardware present - tibia ICD-9 Codes: 824.41, 824.51

Comments:
No Comment 470　470　470　Normal

500

Guidelines — 480　Skip to End　502 — Start Over　430 — Continue

APPARATUS, METHOD AND SOFTWARE FOR DEVELOPING ELECTRONIC DOCUMENTATION OF IMAGING MODALITIES, OTHER RADIOLOGICAL FINDINGS AND PHYSICAL EXAMINATIONS

This patent application claims the benefit under Section 119(e) of the provisional patent application assigned Application No. 60/890,189 and filed on Feb. 15, 2007. The present application is a continuation-in-part application of the currently pending patent application filed on Jul. 30, 2002 and assigned application Ser. No. 10/209,647 (which further claims priority to the provisional patent application assigned Application No. 60/308,771 and filed on Jul. 30, 2001) and therefore claims the benefit of said prior applications according to the provisions of Section 120. The present application is also a continuation-in-part application of the currently pending patent application filed on Jan. 7, 2006 and assigned application Ser. No. 11/326,910 and therefor claims the benefit of said prior application according to the provisions of Section 120.

FIELD OF THE INVENTION

The present invention relates to methods for creating electronic documentation of imaging modalities, other radiological findings and physical examinations, as correlated to a patient's medical history and clinical findings.

BACKGROUND OF THE INVENTION

Proper documentation of medical imaging findings, including anatomical location, joint position, arthritis location with severity, fracture patterns, bone changes, changes from joint arthroplasty, and ICD-9 coding, are a vital aspect of a physician's imaging report. Radiographic data is recorded as an x-ray report for insurance reimbursement and for the patient's medical record. The important outcome data likely ends up in the clinical "black hole" of an individual patient's chart.

Electronic medical records (EMRs) are now finding their way into private practice but these systems offer little in the form of software suites for documenting imaging findings and for generating standard and therefore searchable imaging documentation. While radiological software is available for certain templated studies, there is little in the way of imaging electronic documentation other than templated "pick-lists" for common findings. The currently available systems suffer from one or more of the following shortcomings:

- templates and "pick-lists" range from too simple to complex, creating confusion among the users;
- minimal use of standard nomenclature;
- hardware, software and support is expensive;
- physicians lack time to customize the system;
- physicians lack time to learn a new program, especially a complex one;
- screens are too "busy" and too many windows open at any given time;
- minimal use of published clinical guidelines.

BRIEF DESCRIPTION OF THE DRAWINGS

The present invention can be more easily understood and the advantages and uses thereof more readily apparent when the following detailed description of the invention is read in conjunction with the figures wherein:

FIG. 1 illustrates a user login screen display.

FIGS. 2 and 3 illustrate patient information screen displays.

FIGS. 4 and 5 illustrate examination information screen displays.

FIGS. 7 and 8 illustrate examination information screen displays.

FIG. 14 illustrates a examination finalization screen display.

FIGS. 15-20 illustrate screen displays of as associated with an alternative embodiment of the invention for evaluating fracture patterns.

In accordance with common practice, the various described features are not drawn to scale, but are drawn to emphasize specific features relevant to the invention. Like reference characters denote like elements throughout the figures and text.

DETAILED DESCRIPTION OF THE INVENTION

Figure 4:

Before describing in detail exemplary apparatuses, methods and software for developing electronic documentation of imaging modalities and a patient examination, it should be observed that the present invention resides primarily in a novel and non-obvious combination of elements, method steps and software modules. So as not to obscure the disclosure with details that will be readily apparent to those skilled in the art, certain conventional elements have been presented with lesser detail, while the drawings and the specification describe in greater detail other elements pertinent to understanding the invention.

The following embodiments are not intended to define limits as to the structure of the invention, but only to provide exemplary constructions. The described embodiments are permissive rather than mandatory and illustrative rather than exhaustive.

The system of the present invention is faster and more complete than a prior art dictation-transcription system for recording radiological and physical examination findings and generating patient records. The system also provides complete and accurate coding and documentation of physical examination and radiological findings using standard nomenclature, which is especially useful for CMS and other insurance reimbursements. This format is especially useful in long term studies, clinical trials and medical record searches during retrospective studies. Use of the software documentation package embodying the system of the invention and the standard nomenclature that it offers also enhances communications between radiologists, specialists, and non-specialists when describing fracture or disease findings in out-patient ambulatory, in-patient and emergency room settings. With multiple physicians recording the same (standardized) fracture pattern or arthroplasty findings in the same nomenclature, x-ray and physical examination reports are recorded in a standard manner, thus making all reports text searchable. Findings and results can be stored in simple, ASCII format to facilitate searching and transfer to other formats such as PDF, XML and databases.

To relieve the practitioner of transcription, documentation and coding headaches and attendant dictation, transcription and coding costs, and to provide better and more efficient utilization of data that is recorded according to known medical examination techniques, a web-based version of the system of the present invention records and codes the results of skeletal and anatomical findings. The system also records the results of fracture healing and changes associated with orthopedic implant survivorship. These findings are also recorded in the form of a searchable and standardized radiological database for later use in anonymous fracture studies and joint replacement registries.

Currently, the orthopedic community must rely on small, long term orthopedic studies or foreign joint registries that are often based on secondary data gleaned from the original chart or culled from hospital CMS data. Also, in most cases, existing joint registries record findings at only three time points: initial joint replacement, revision joint replacement and patient death. A web based radiographic registry derived from the present invention collects radiographic data at other time points to allow for earlier post-market surveillance of implants or treatment failures. Recording skeletal x-ray findings in a standard nomenclature is also useful for the studying healing of specific fracture classifications, medical device implant tracking (for post-market surveillance), identification of patients who may need earlier follow-up evaluation and ultimately searches of medical records for retrospective studies. Use of the system of the present invention will also help to improve communication between the musculoskeletal specialist and non-specialist when describing and coding skeletal radiographic changes in both in-patient and out-patient settings.

To aid the user with the physical examination and radiological evaluation, the invention comprises a plurality of simple skeletal line drawings and anatomical renderings and photographs of different parts of the body. In one embodiment the renderings and photographs are segregated by anatomical section and include the spine, upper extremity, hand and wrist, lower extremity, foot and ankle and pelvis. The renderings of the skeletal areas are color coded or otherwise represented to divide individual bones into proximal inter-articular, distal inter-articular and shaft fractures. Expected fracture patterns, possible bone changes (e.g., expected changes that would be observed for the fracture and its location), as well as bone changes around joint arthroplasty and other implants are given for each section of the bone or joint. The amount of healing or lack of healing is noted and recorded for later use, including in a clinical registry.

Generally, the renderings of the present invention are responsive to movement of a cursor over the bone section of interest. Various organ systems and other anatomical areas can be displayed and color coded in a like manner. The system is compatible with all CCHIT EMR'S (electronic medical records) and provides links to ACR (American College of Radiology) guidelines at www.guidelines.gov.

One embodiment the system is web-based, so that the user incurs minimal hardware and software costs. ICD-9 coding (including the specific digit when appropriate) is automatic and based on the entered findings, including fracture pattern, arthritic changes, hardware failures and joint pathology. If any findings are erroneous or examination steps omitted an error or alert message is generated and displayed on the user's screen. The system includes a knowledge base for generating the examination steps and guidelines and also to make information available to the patient, non-specialist and specialist alike. For patient's facing implant surgery, the system includes web links to device manufacturers' patient information web site. Web links to device manufacturer's physician education information are also provided. The knowledge base can also be used for patient education and to present clinical reminders and clinical decision support to the physician. The EMR's generated by the system are immediately available (no waiting for transcriptions) in electronic or printed form and can also be emailed (e.g., in HTML format) to the patient (or the patient given a hard copy) the attending physician, the referring physician and the insurance carrier. Because the nomenclature and examination steps are standardized, the findings are easily searchable.

The findings are anonymously presented in the transcript since the patient's name does not appear in the report; only a patient number appears. The physician maintains a record that cross-references the patient number to the patient's name. Thus patient confidentiality is maintained. X-rays, MRIs, bone scans and other imaging findings are saved with names/titles that include no patient identifying data other than a system record number for use in an anonymous registry, such as a fracture registry, an arthroplasty registry, a tumor registry and other important data storage sites.

Generally, the system is usable by anyone with some medical training. The system is relatively simple and straightforward so that one lacking rigorous and detailed physician/medical training, such as a nurse or nurse's assistant, can conduct at least the initial physical examination and input the findings.

In the web-based embodiment of the invention, links to American College of Radiology Clinical Guidelines (as well as other web-based clinical guidelines) are provided. The system user may find such guidelines useful for evaluating the patient's diagnostic, physical and imaging findings.

The invention will be described in the context of a web-based version, although those skilled in the art recognize that a software program offering identical capabilities can be stored locally and executed to present the same capabilities. To begin the session, the user enters a user name and password in text boxes 12 and 13 of FIG. 1 and verifies that he/she is an authorized user by clicking (selecting) the "Verify Login" button (or active text box) 15. As the case with most of the other buttons in the program, when the user rolls his cursor over the button 15, the button turns green, giving visual feedback indication that the cursor is over the button. Clicking in the green area for the "Verify Login" button causes the system to verify the user's login information.

The user can open any of the presented windows, including: overview (presenting an overview of the software program), sponsor (identifying sponsors and their web sites), subscribe (prompting the user to enter subscription information to subscribe to access to the Automated MD web site), references (listing web-based or book references), index and support (to request support for use of the system). In one embodiment, only the transcript generation process requires a successful login; the other buttons can be selected absent a successful login. A "Review Transcripts" button 17 is grayed-out in the display until the user has successfully logged in.

FIG. 2 depicts a next screen 29 that appears after the user has been verified. The user is prompted to enter and confirm patient identification information in boxes 30 and 32. To maintain patient anonymity, the identification information is typically a number, which may be a patient's identification number that the physician's office uses to track the patient internally. Patient's date of birth information, her chief complaint and any available implant information is indicated in the respective drop down box 34 and the text boxes 36 and 38. Additional visual (color-coded) feedback information is provided by identifying the button the cursor is over (a blue or green color) and the buttons the user has previously clicked to enter information (a red color).

Next the user selects one response from each of the radio buttons: type of appointment 40, type of injury 42, symptoms duration 44 and symptoms progress 46. Additional comments can be added in a scrolling text field 48. Upon finishing the screen 29 the user clicks the continue button 50. Note the user can also start with a new patient by clicking a button 52, review previously stored transcripts by clicking a button 54, close the window by clicking a button 56 and log out by clicking a button 58. Clicking the "New Patient" button 52 displays a warning message that the entire foot examination transcript for the current patient will be deleted and a transcript for a new patient started. If the "Review Transcripts" button 54 is clicked, all of the previously stored transcripts are listed in a new window and the user can select from the list.

Figure 3:
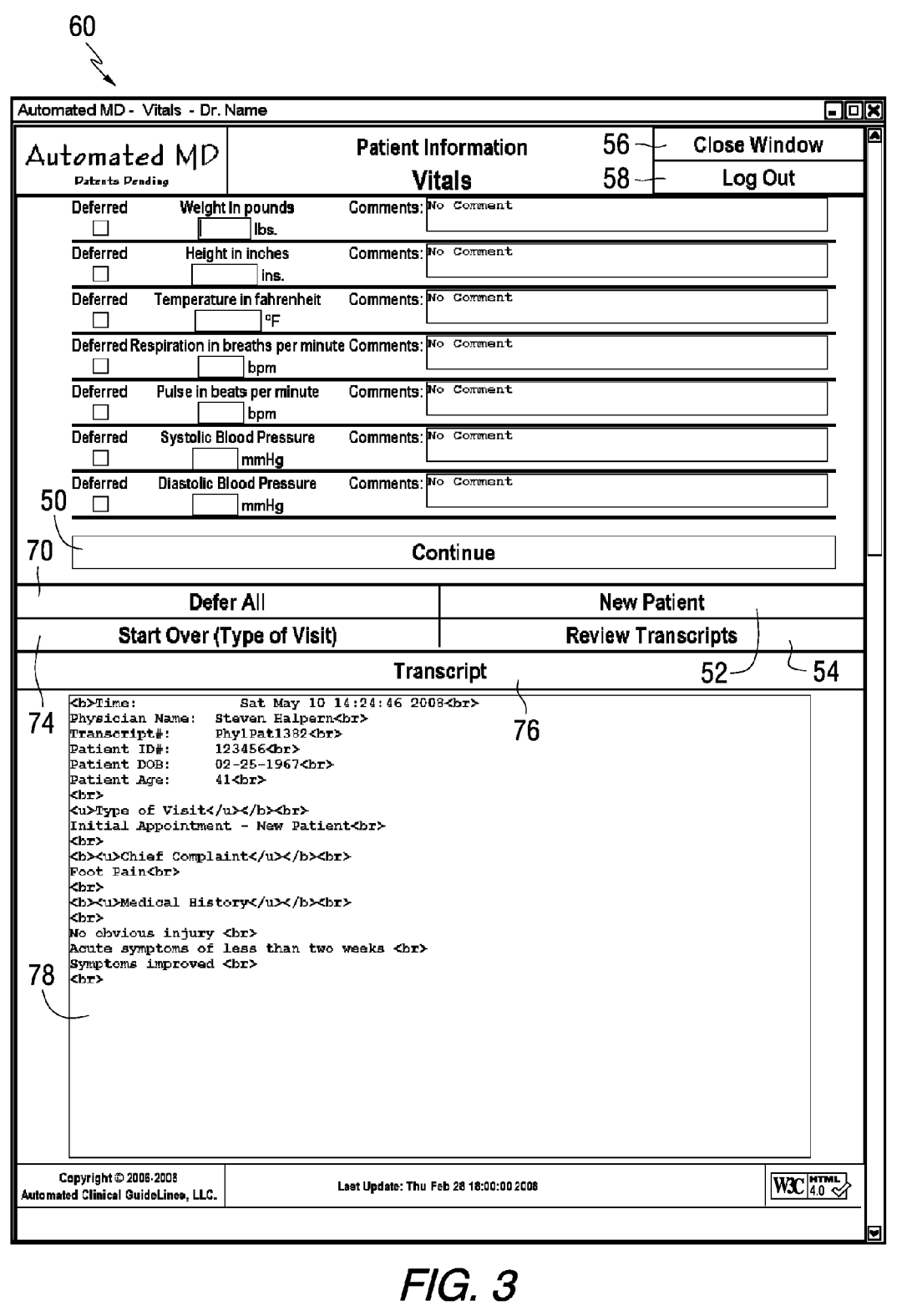

FIG. 3 represents a screen 60 that requests vital signs information, including weight, height, temperature, respiration, pulse, systolic and diastolic blood pressures. Comments can also be provided for each of the vital sign readings as indicated. In the event any vital sign is outside a range that is considered normal for the given reading, the system presents a warning that the vital sign may indicate a health issue. The patient should follow-up any such warning with a physician. Alternatively, the vital sign measurements can be deferred to a later time by checking each deferred button to the left of the vital signs information or by selecting the "Defer All" button 70. The user can also begin entering data for a new patient by clicking the button 52, review previously stored transcripts by clicking a "Review Transcripts" button 54 or start over (type of visit) by clicking a "Start Over (Type of Visit)" button 74, which will cause the system to prepopulate the display screens with previously entered type-of-visit information. Clicking the button 74 also displays a warning that the entire transcript of the current foot exam process will be deleted and a new transcript started. The user is requested to either cancel the previous entry by clicking a "Cancel" button or acknowledge the previous entry by clicking an "OK" button. If the user clicks the "OK" button, the transcript information from previous examinations is presented below a heading 76 in a window 78. If the user clicks the "Cancel" button, the transcript information from the current examination is presented below the heading 76. The user continues by clicking the continue button 50.

FIG. 4 presents a screen 90 that identifies (in text form) the various anatomical regions of the body. The user selects a region based on the patient's complaint. The "Foot Exam" button 92 is selected for the purpose of describing the invention, but the select buttons associated with the other anatomical regions function similarly, Successive clinical examination screens and radiographic examination screens allow the user to enter data by clicking radio buttons, checking check boxes or as free form text in a comment area. The transcript of the examination steps conducted to this point is set forth in the window 78 of FIG. 4.

Figure 5:
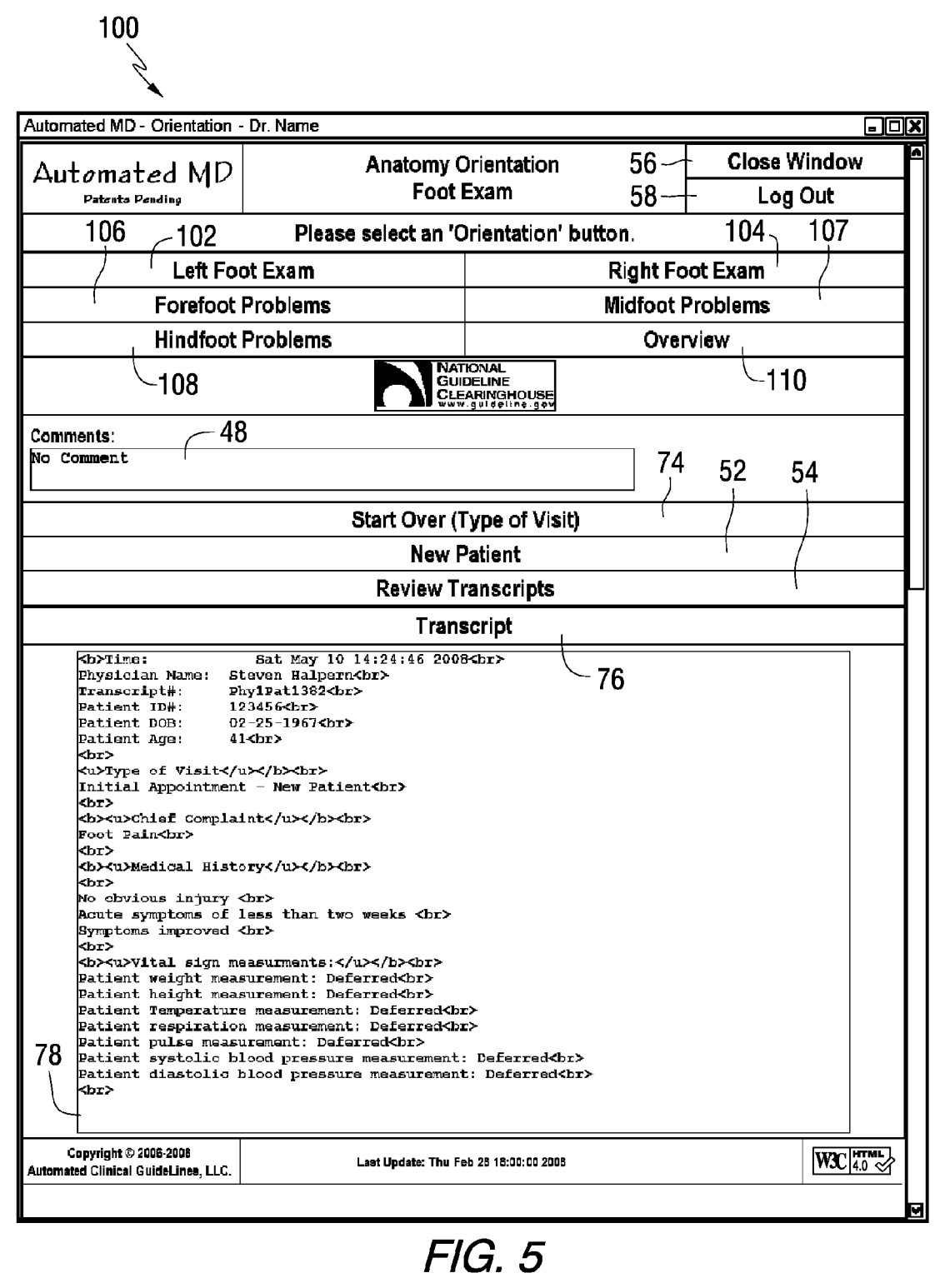

A screen 100 illustrated in FIG. 5 presents various anatomical orientations of the foot in a designated button, including left foot exam 102, right foot exam 104, forefoot problems 106, midfoot problems 107, hindfoot problems 108 and a general overview of the foot anatomy 110. The buttons associated with the labels "Forefoot Problems," Midfoot Problems," "Hindfoot Problems" and "Overview" provide anatomical and medical information to the user; only the left and right foot exam buttons 102 and 104 will continue the examination process and the entry of examination findings.

Figure 6:
FIG. 6 illustrates a medical history screen display.

Selecting the "Left Foot Exam" button 102 (selecting the "Right Foot Exam" button 104 proceeds through similar screens) displays a screen 120 of FIG. 6, allowing the user to select one or more of the entries in the window 130 of checkboxes or the "No Identifiable Symptoms" check box 132. The screen 120 continues to either a physical examination when the user clicks a button 136 or to an image evaluation when the user clicks a button 138.

Figure 7:
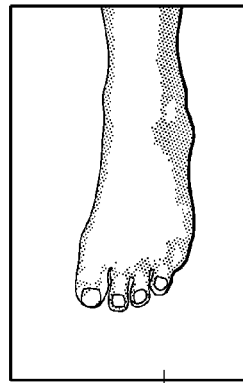

Assuming no identifiable symptoms are present and the user selects the physical examination button 136, next a "Foot Exam (Left), Anterior View, Standing" screen 140 is displayed as shown in FIG. 7. A required selection of one of the radio buttons in the alignment, position and medial curvature boxes 144, 146 and 148, captures data for the medical record (transcript). A photograph or other image 150 of the foot is also displayed to aid the user. The user can click an "All Normal" button 152 or a "Defer All" button 70 to proceed to the next screen without having to click individual radio buttons in the boxes 144, 146 and 148. The user can also opt to suspend the remaining physical examination tests and move to the image examination by clicking a "Skip to Image Exam" button 154, which deletes only the present physical examination transcript information and permits the user to continue with generation of an image examination transcript.

The examination can be aborted by clicking an "Abort Exam" button 156, requiring the user to enter a reason for aborting the examination in the comment field 48. Clicking the button 156 causes the system to skip to the end of the physical examination where the user can either add an electronic signature to the transcript or proceed to the image examination. A "Start Over (Physical Exam)" button 158 is not available to the user (the button is grayed-out) when the user begins the physical examination. Later, when the examination is underway, the button 158 is available and clicking the button displays a warning box advising that the foot exam process will be restarted, the transcript of the current foot exam process will be deleted and a new physical examination transcript will be initiated. In the warning box the user is requested to either cancel the previous "Start Over (Physical Exam)" entry by clicking a "Cancel" button or acknowledge the previous entry by clicking an "OK" button.

Figure 8:
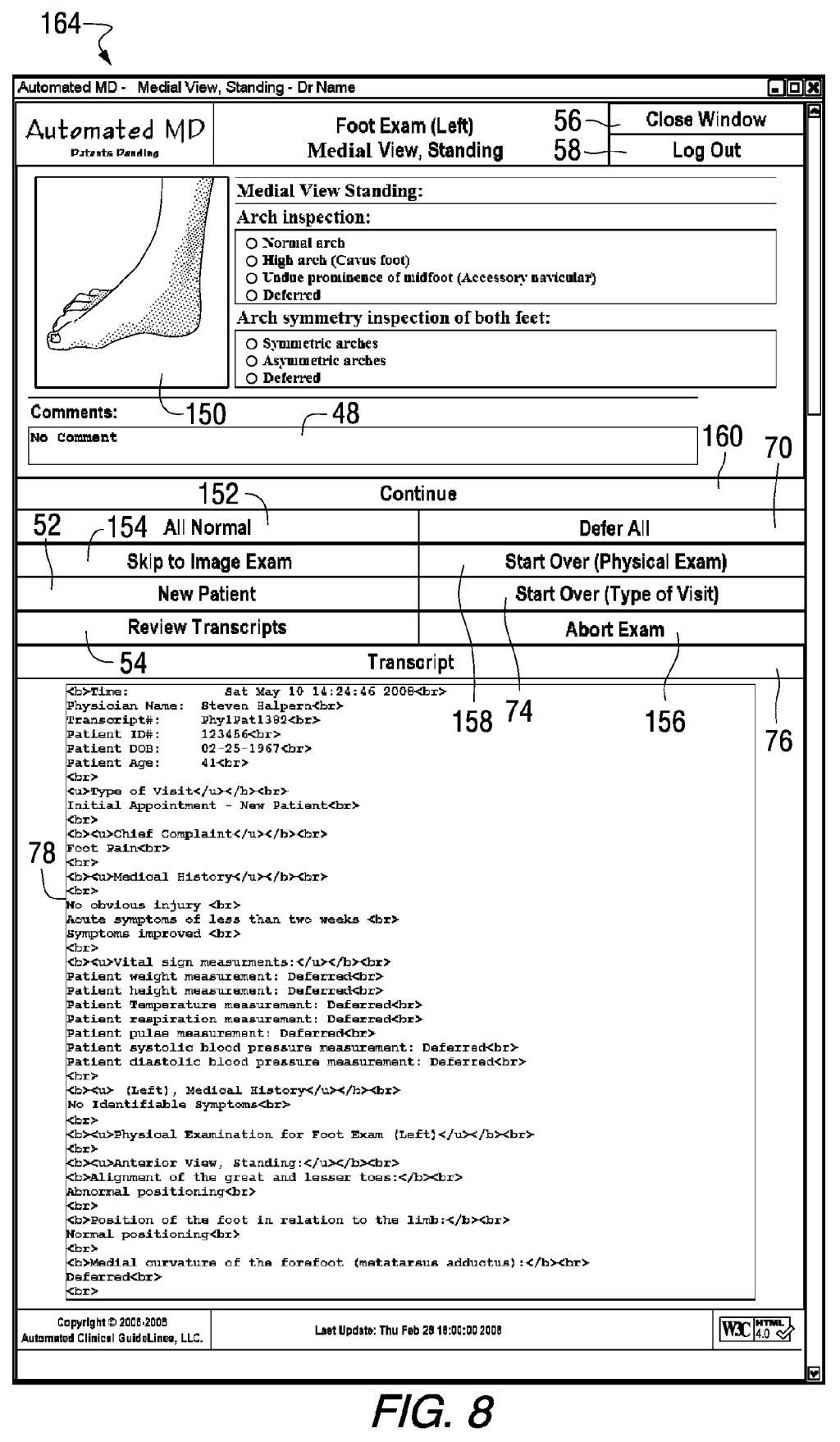

Selecting a "Continue" button 160 takes the user to a next screen 164 (FIG. 8) entitled "Foot Exam, Left/Medial View, Standing" in the foot examination process. Here too, like the screen 140 of FIG. 7, the user is asked to indicate whether the findings are all normal (the button 152) or to be deferred (the button 70). At each successive step of the foot examination, the user will also be asked to indicate whether the findings are all normal or are to be deferred until later.

The user continues identifying the examination findings at each screen by selecting appropriate radio buttons, checking appropriate check boxes, deferring any or all of the examination steps or indicating that all the findings are normal. The user can also select one of the presented text boxes/buttons 52, 54, 74, 154, 156 or 158 to diverge from the selected examination process steps.

For the selected left foot examination (or the right foot examination), the examination proceeds to the following examination stages, each presented as a separate display screen following the medial view (standing) examination screen 164 (FIG. 8) described above: lateral view standing, posterior view standing, standing on toes, gait, angle of gait, medial malleolus, sesamoid, MTP joint, ankle dorsiflexion, ankle plantar flexion, inversion and eversion, supination and pronation, great toe at zero starting position, posterior tibialis, anterior, tibialis, peroneeus longus and brevis, extensor hallucis longus, flexor halucis longus, anterior drawer test, varus stress test, MTP instability, interdigital (Morton) neuroma test, sensitivity test, Thompson test and squeeze test. Each screen for these subsequent examination stages comprises radio buttons and/or check boxes for entering observed findings and a comment box. The transcript is updated responsive to the selection of the radio buttons, check boxes or the addition of comments on each screen.

Certain of the photographs presented during the physical examination stages include aids for the user conducting the examination, including angular degree indications for ankle flexing and arrowheads for indicating foot movement directions.

In lieu of entering the physical examination findings, the user can defer one or more of the examinations stages presented on each screen by checking the appropriate check box. All examination findings presented on a screen can be deferred by selecting the "Defer All" button 70, which then causes the next examination screen to be presented. Clicking the "All Normal" text box/button 152 also automatically displays the next screen. Thus both the "Defer All" and the "All Normal" buttons also act as "continue" buttons for the system.

Generally, whether the user defers certain physical examination steps, indicates that certain steps reveal abnormal findings or indicates that all examination findings are normal, the system of the invention proceeds to display each successive screen/examination stage to generate the transcript.

Figure 9:
FIG. 9 illustrates a completed transcript screen display.

After the physical examination of the foot has been completed, the final physical examination transcript is presented in a screen 170 of FIG. 9. Various options are presented to the user on the left side of the screen 170. The user can continue by clicking one of the presented buttons to return to a prior screen or continue to a different area of the system of the present invention. The presented areas include, the "Type of Visit" button 74, A "Symptoms" button 172, a "Vitals" button 176, an "Examination" button 178, a "Fracture Selection" button 180, an "Impression" button 182, a "Plan" button 184, a "Treatment" button 186, a "Finalize" button 188 and a "Close Window" button 190. In one embodiment, the impression report, the plan report and the treatment recommendation provide the pertinent information based on the physical examination and the x-ray findings.

Figure 10:
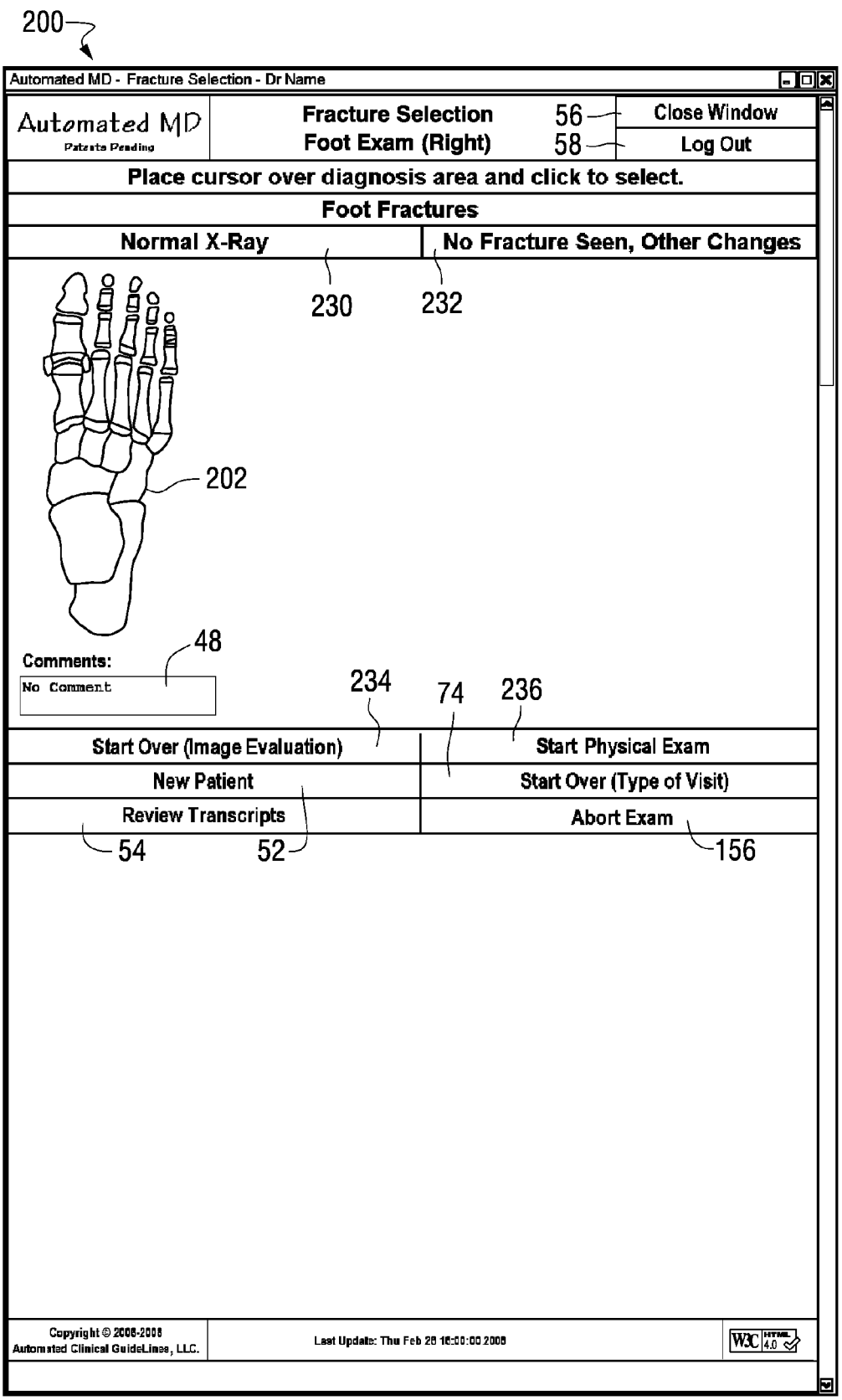
FIGS. 10, 11 and 12 illustrate fracture selection screen displays.

FIG. 10 illustrates the first screen 200 displayed for the image evaluation portion of the examination. After the image evaluation has been completed a final transcript including both the physical examination findings and the image (e.g., x-ray) evaluation, is generated as described below.

Figure 11:
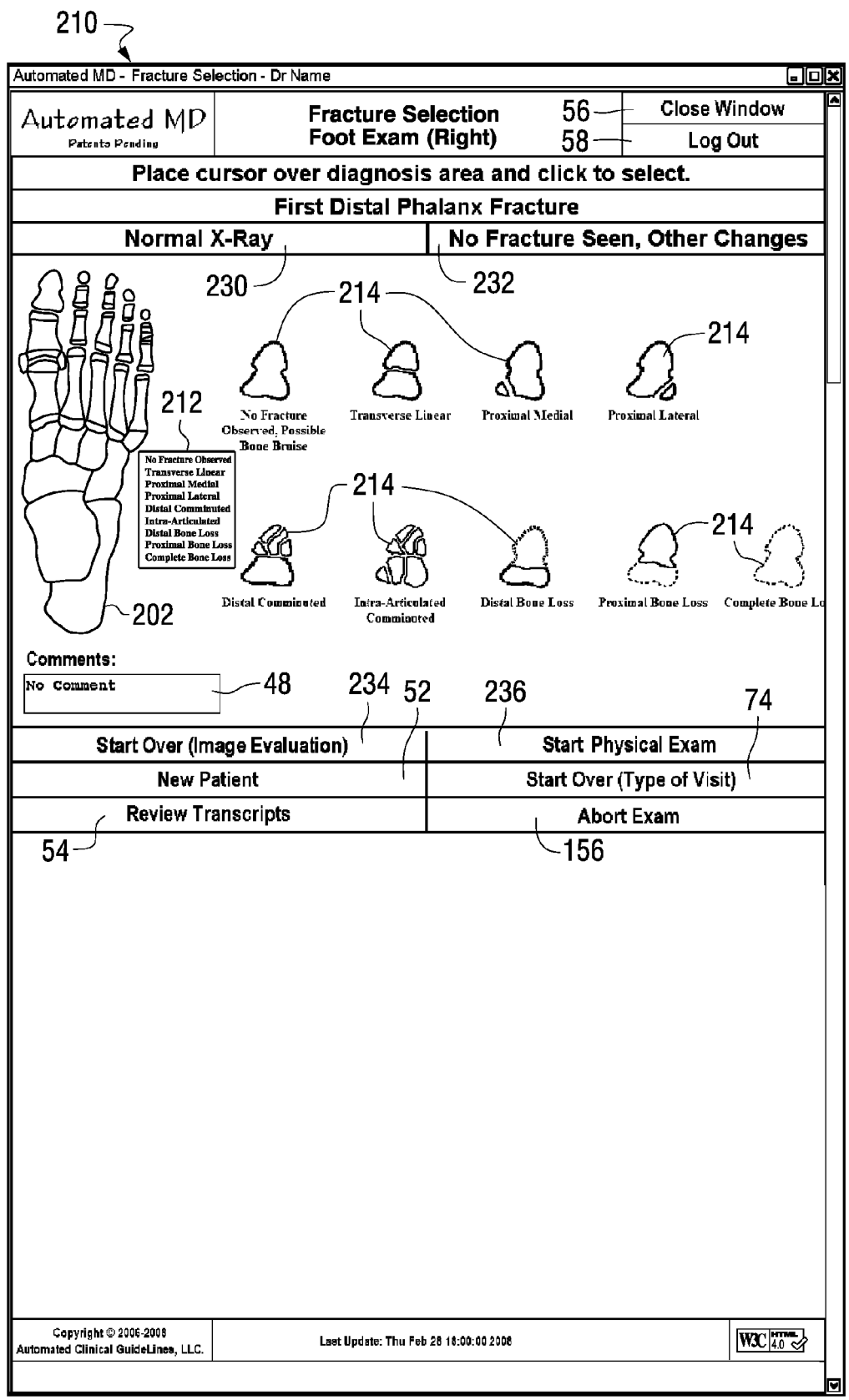

The screen 200 illustrates an image of the individual bones of the selected right foot 202. Rolling the cursor over each bone of the foot image displays a menu of the possible fractures (or bone loss) for that bone and to the right of the foot displays multiple renderings of the selected bone, each rendering depicting the bone with the indicated fracture (or bone loss). FIG. 11 illustrates a screen 210, including a menu 212 displayed as the user rolls the cursor over a selected bone (in this example, the first distal phalanx), and the fracture/bone loss renderings 214 for each listed item in the menu 212 for the first distal phalanx. The fracture/bone loss title from the menu 212 is displayed under each rendering 214. Different menu items and different renderings are displayed for each bone of the foot.

Figure 12:
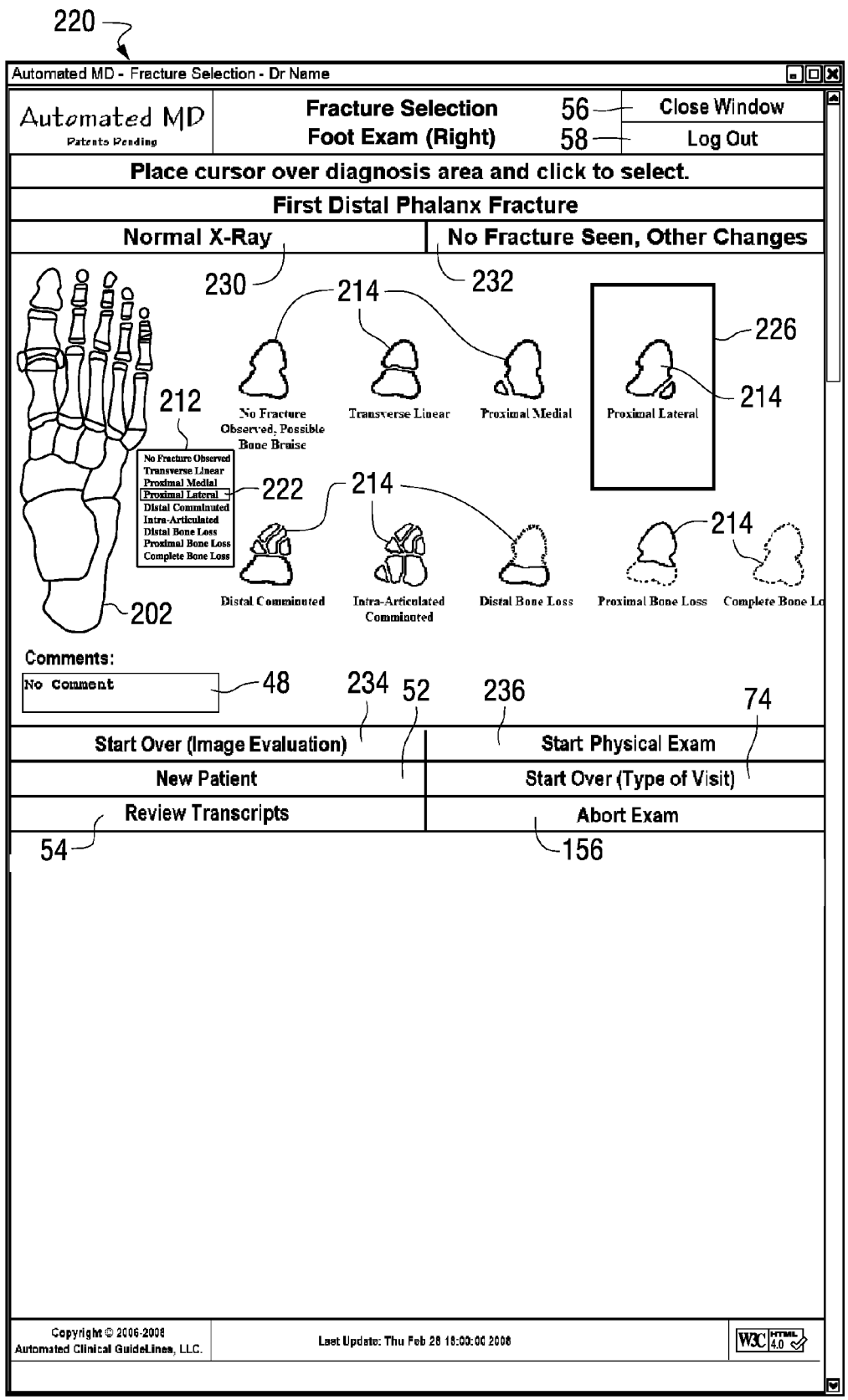

To conduct the image evaluation portion of the examination, the user consults the patient's x-ray image, selects the appropriate fractured bone, rolls the cursor to that bone in the right foot image and selects the fracture/bone loss for the selected bone from the presented list. The multiple bone renderings, each showing a different fracture pattern or bone loss, aid the user in identifying the fracture/bone loss observed in the x-ray. FIG. 12 depicts a screen 220 indicating that the user has selected a "Proximal Lateral" fracture 222 (shown highlighted in the menu 212). Also, the rendering 214 of the "Proximal Lateral" fracture is highlighted by a box 226 surrounding the rendering 214.

If no fractures are observed in the x-ray image, the user selects a "Normal X-Ray" button 230 (in the screen 200 of FIG. 10) for a normal x-ray or selects a "No Fracture Seen, Other Changes" button 232 if there are no observable fractures but other changes are observed in the selected foot bone.

The user can also start the image evaluation again by clicking a button 234 at the bottom of the displayed screen 200. The user can also opt to begin the physical examination by clicking a button 236.

Groups of bones of the body (e.g., the ankle, the spine) are displayed similar to the display of the foot bones in FIG. 10. Rolling the cursor over the bones causes a menu to be displayed and one of the renderings to be highlighted as illustrated in FIGS. 11 and 12.

Figure 13:
FIG. 13 illustrates a fracture evaluation screen display.

After a specific bone and specific fracture/bone loss pattern are selected, as described relative to the FIGS. 10-12, a fracture evaluation screen 250 is displayed as depicted in FIG. 13. The extent of displacement is entered by checking a radio button within a displacement window 258 and the extent of fracture healing is entered by selecting a radio button within the fracture healing window 260. The user also selects one or more of the applicable check boxes within the special conditions window 262 or indicates that no special conditions are present by checking the "No special considerations" box in the window 264.

Arthritic conditions are indicated by selecting from the various drop down menus 270 in a window 272. The severity of the arthritis at each of the indicated joints is identified by selecting a quantitative or qualitative (e.g., mild, moderate, severe, joint fused) value from each drop down menu 270. As illustrated, different arthritic condition severities have been selected from the drop down menu for different illustrated joints within the window 272.

Additional fractures can be evaluated by clicking a button 280 or the user can continue by clicking on a button 288, which provides links to pertinent medical information, differential diagnoses, other pertinent considerations, possible adverse effects of the fracture and possible adverse effects of any treatment, referrals to other physicians and the desired minimum time until an appointment with the recommended physician (red flags), etc. Links to medical records of other patients with similar medical issues are also provided.

If the user selects the "Finalize" box 188 of FIG. 9, either after the physical examination or the x-ray evaluation or both have been completed, a screen 300 of FIG. 14 is displayed. Additional image data or anatomy data can be entered by clicking respective boxes 302 or 304. To add a time-stamped electronic signature and electronically sign the transcript, the user selects the "Electronic Signature" button 308. The user's username and password are requested in boxes 312 and 314, respectively, and required prior to electronically signing the transcript. The transcript to be signed is displayed in the window 78.

According to another embodiment of the invention, to begin the patient evaluation and findings documentation process, a system user analyzes a patient's x-rays or imaging studies and then enters corresponding information into the system, as described below. The system documents the findings and generates the patient's record for bone and joint findings as well as other disease findings throughout the body.

Figure 15:
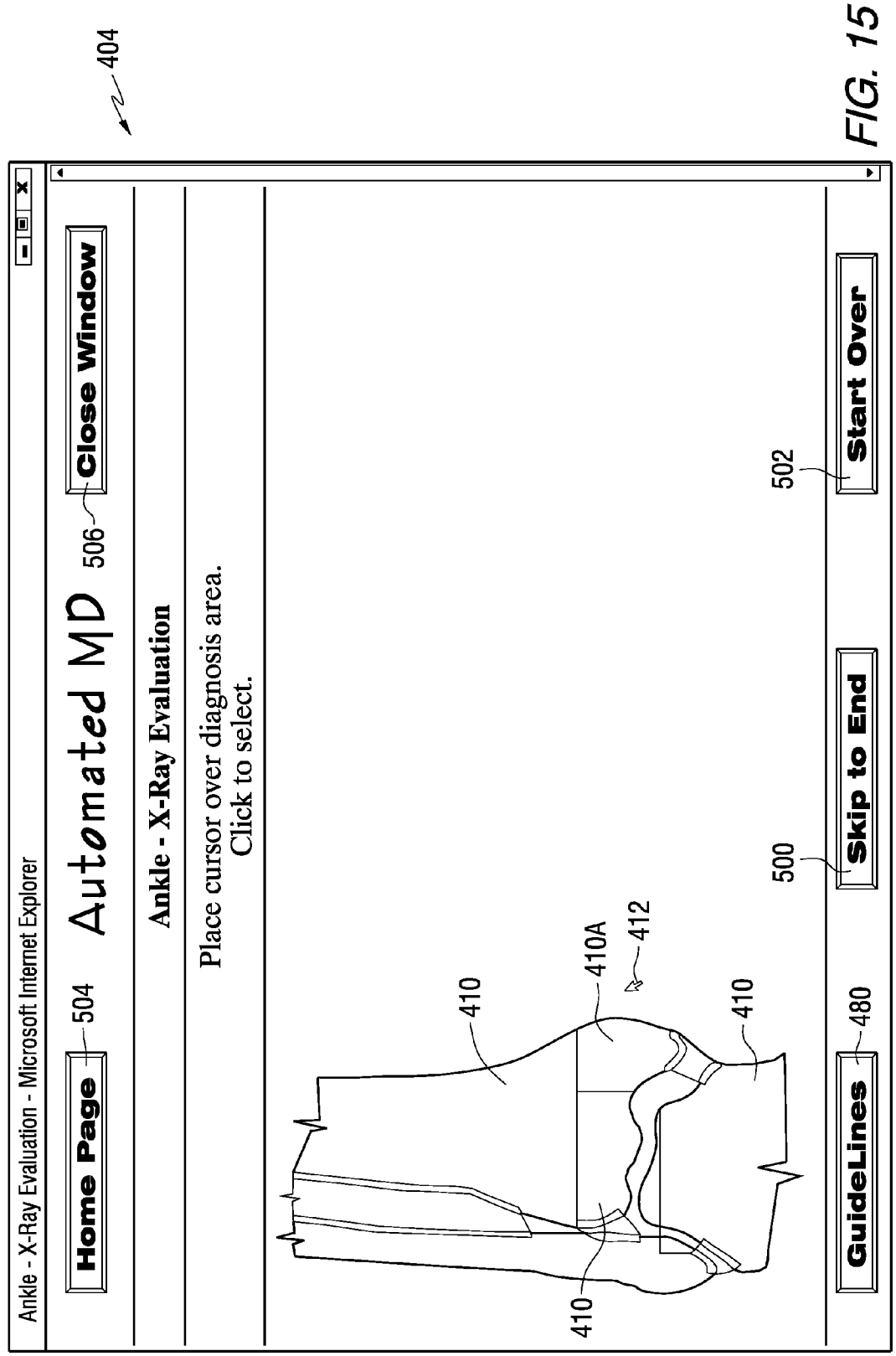

By way of example, assuming the patient has suffered an ankle injury, the user instructs the system to display the ankle region. FIG. 15 depicts a screen display 404 of an ankle subdivided into a plurality of anatomical diagnostic regions 410 and a cursor 412. Upon determining a specifically affected ankle region from a patient's x-ray, the user rolls the cursor 412 over the affected region 410 to display a detailed view of the possible fracture patterns and bone changes associated with that region.

FIG. 15 also depicts a "Skip to End" button 500, a "Start Over" button 502, a "Home Page" button 504 and a "Close Window" button 506. These buttons control the system as indicated by the button title.

Figure 16:
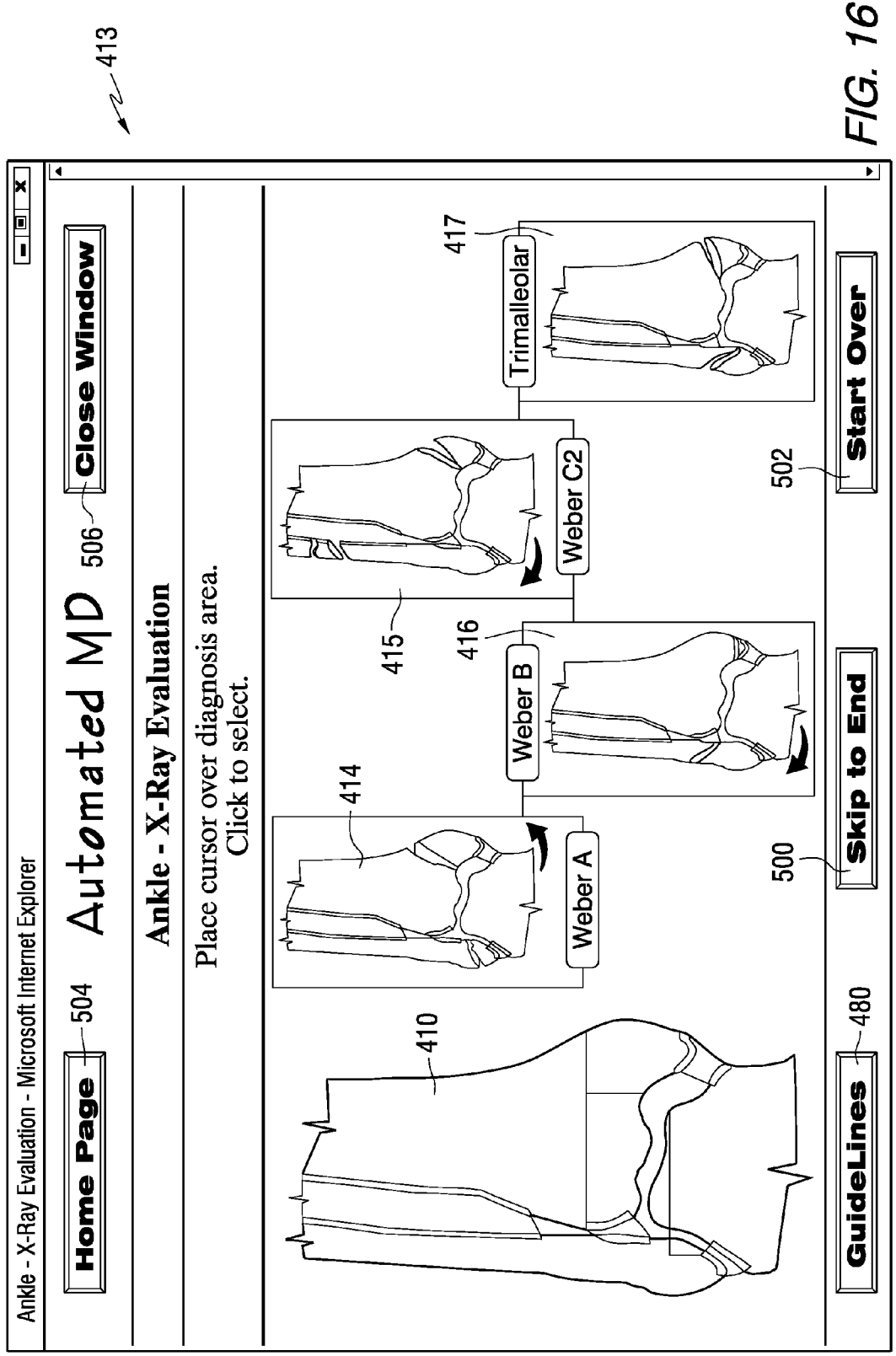

FIG. 16 illustrates a screen display 413 including detailed views 414, 415, 416 and 417 of the region 410A of FIG. 16. The detailed views are generated when the user rolls the cursor over the region 410A. The detailed views also identify the fracture patterns and bone changes by name. Rolling the cursor over an area of interest and displaying additional information responsive to the area rolled over is referred to as graphical or visual feedback.

Figure 17:
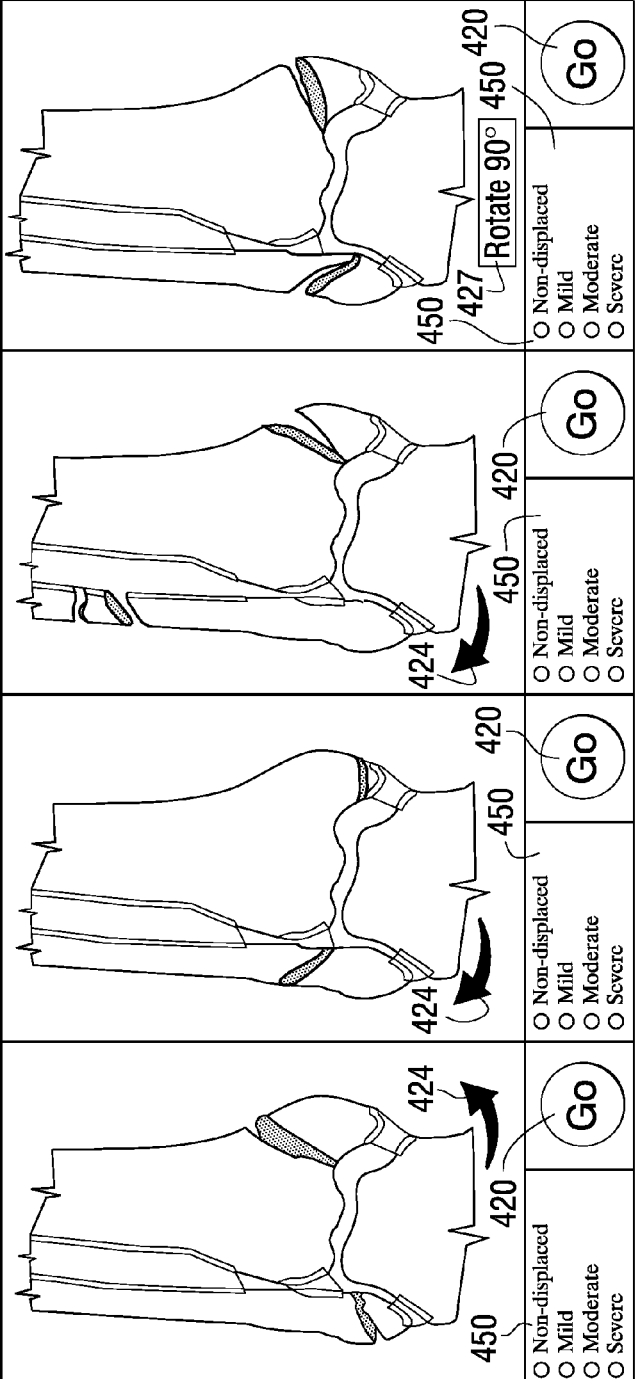

A mouse click in the selected region 410A of FIG. 15 calls and displays a screen display 425 illustrated in FIG. 17, including a rendering and a textual description of the four possible fracture patterns and the ICD-9 code for each one, as illustrated in screen display regions 425A, 425B, 425C and 425D. In FIG. 17 the illustrated fracture patterns include specific fracture or disease classifications such as Weber A, Weber B, Weber C2 and Trimalleolar fracture patterns. Activation of the "Rotate 90° " icon 427 associated with the Trimalleolar fracture provides a rotated view of that fracture pattern. In the case of an ankle fracture, the ankle is divided into the following anatomical sections: intra-articular distal tibia fractures, intra-articular distal fibula fractures, lateral malleolus fractures, medial malleolus fractures, and talar dome fractures, although all such fracture patterns are not illustrated in the FIGS. 16 and 17.

The ICD-9 codes set forth in FIG. 17 include options for closed (824.41) and open (824.51) fractures. From one of the FIG. 17 screen display regions 425A, 425B, 425C and 425D the user selects from a radio button window 450 to indicate the degree of severity of the patient's fracture. Arrowheads 424 in FIG. 17 indicate the direction in which the ankle injury occurred. Subsequent activation of a "GO" button 420 brings up a next screen illustrated in FIG. 18.

Figure 18:
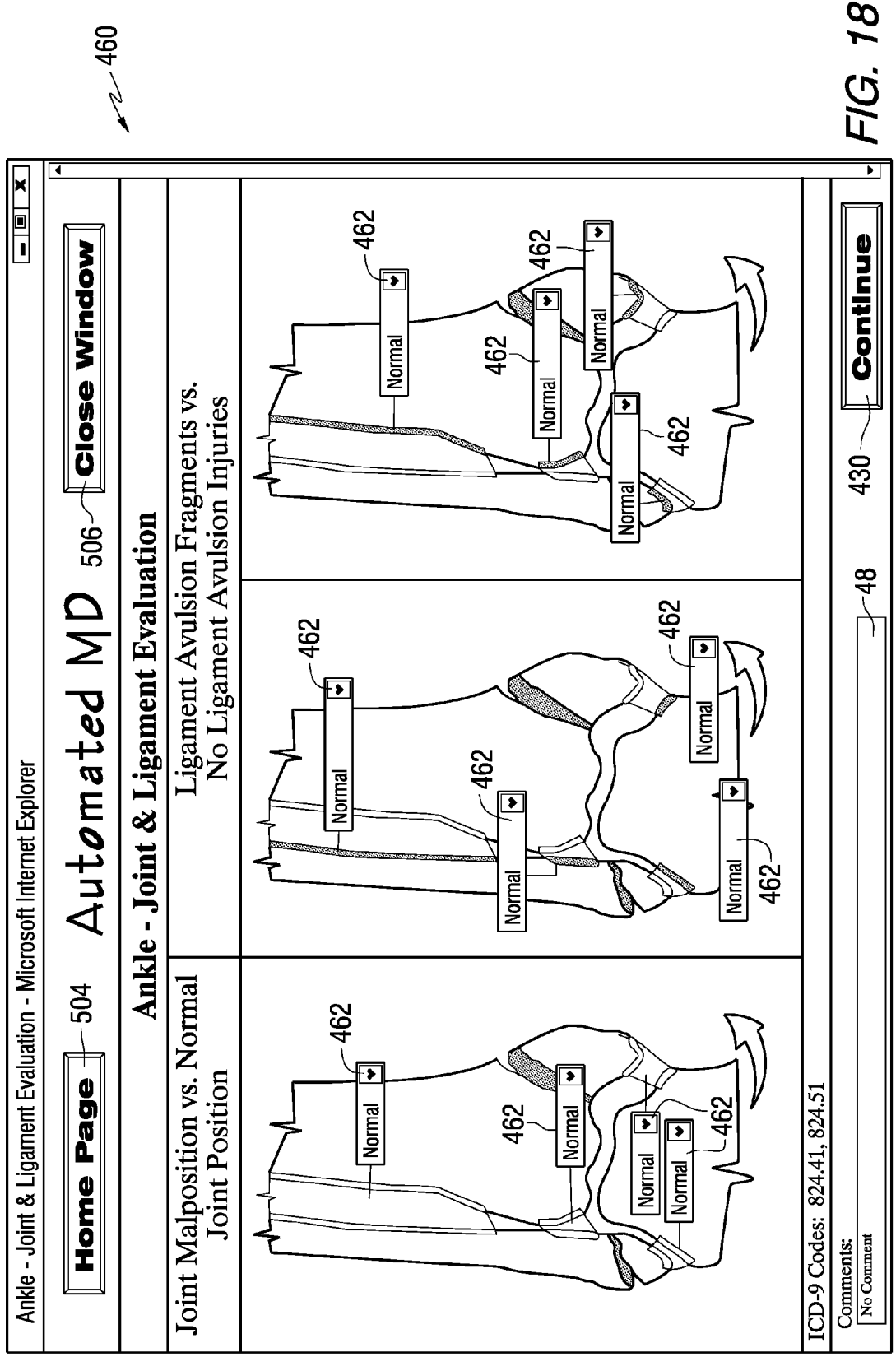

FIG. 18 depicts the next screen 460 responsive to the user's selection of the Weber A fracture pattern. The screen display 460 prompts the user to enter descriptive information responsive to joint position and ligament injury evaluations by selecting an appropriate descriptor from the various drop down menus 462, with each menu associated with a different anatomical region as indicated by a pointer extending from the drop down menu 462. In the illustrated FIG. 18 embodiment the various drop down menus 462 are distributed across multiple renderings of the region of interest to declutter the display.

After all appropriate choices have been made in the FIG. 18 the drop down menus 462 (alternatively, check boxes can be presented for making the required selections), the user clicks a continue button 430 to display the next screen, that is, FIG. 19.

The FIG. 19 screen display 466 prompts the user to conduct an arthritis evaluation of the patient's x-rays, with responses entered according to drop down menus 470. In one embodiment the arthritic conditions for the three indicated regions are characterized as normal, mild, moderate, severe or joint fused.

The FIG. 19 screen display 466 also prompts the user to evaluate certain special considerations and enter the findings in check boxes 472 that reflect the observed conditions or values. Exemplary conditions include ligament/bone connectivity and joint widening conditions.

Certain of the displays described above include a guidelines hyperlink 480. If the processing system running the system software provides Internet access, activation of the guidelines hyperlink directs the user to a web site such as www.guidelines.gov to access the American College of Radiology Clinical Guidelines. Hyperlinks to access other clinical resource web sites such as specialty societies, vendor information sites or educational links are also available according to the present invention. In each case, the displayed web sites and reference information is related to the findings presented in the transcript. For example, if the patient's condition merits a calcaneous plate implant, the physician and the patient are directed to reference information and web sites regarding a calcaneous fracture and the plate implant.

Figure 20:
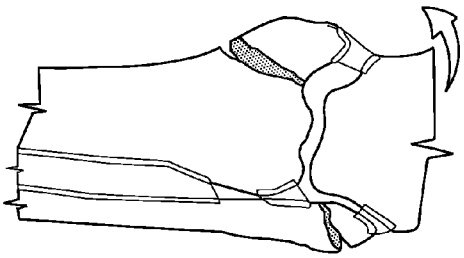

Following completion of the evaluations set forth in FIG. 19, a finalize button (not shown in FIG. 19) is activated to generate the final findings document that captures the menu entries, check boxes, ICD-9 codes, etc. as selected by or presented to the user during the evaluation and data entry processes described above. The final document presented by the system comprises an electronic record with a digital signature of the physician. The document can be printed, stored or transferred to the physicians electronic medical record or the patients electronic health record. A portion of such a final document 478 is illustrated in FIG. 20.

As described, the system, method and apparatus of the present invention are unique and non-obvious for generating an electronic medical record. Although the invention has been shown and described with respect to certain preferred embodiments, it is obvious that equivalent alterations and modifications will occur to others skilled in the art upon reading and understanding this specification and the annexed drawings. In particular regard to the various functions and attributes performed by the above described elements, these are intended to correspond to any element that performs the specified function of the described element (i.e., that is functionally equivalent), even though not structurally equivalent to the disclosed structure. In addition, while a particular feature of the invention may have been disclosed with respect to only one of several embodiments, such feature may be combined with one or more other features of the other embodiments as may be desired and advantageous for any given or particular application.

What is claimed is:

1. A system for guiding a user's examination of a patient and for generating a transcript, the system comprising:
  a processor in communication with an output display device and a user interface, the processor programmed to output to the display device:
  (a) a screen requesting patient identification information, wherein the patient identification information excludes a patient name and further requesting patient medical history information;
  (b) a screen requesting vital signs information;
  (c) a screen presenting a plurality of symptoms in text form, wherein the user can identify one or more observed symptoms as selected from among the plurality of symptoms or the user can indicate that no symptoms are observed;
  (d) in response to the user identifying one or more observed symptoms, a screen presents a plurality of anatomical regions for examination, the plurality of anatomical regions presented in text form, wherein the user selects an anatomical region based on the one or more observed symptoms;
  (e) a screen presents anatomical subregions within a selected anatomical region, the anatomical subregions presented in text form, wherein the user selects an anatomical subregion based on the one or more observed symptoms;

(f) a plurality of screens displays a rendering of the selected anatomical subregion and possible findings associated with a condition of the patient as related to the selected anatomical subregion, the renderings depicting normal and abnormal conditions of the selected anatomical subregion to assist the user with selecting one or more findings, and wherein the computer presents more-detailed renderings responsive to the user rolling a cursor over regions of the renderings;

(g) wherein as the user selects findings, additional renderings are presented related to the selected findings;

(h) wherein one or more of the screens include an icon for allowing the user to switch from the physical examination to an examination of a radiographic image, the processor for receiving user selections from the user interface and generating a patient transcript responsive to information entered into the screens (a) through (h).

2. The system of claim 1 wherein the patient transcript includes information regarding a selected rendering that best describes a patient's condition, the selected rendering using standard nomenclature.

3. The system of claim 2 wherein the renderings comprise skeletal line drawings, anatomical images and photographs.

4. The system of claim 2 wherein the user consults patient diagnostic test results and compares the diagnostic test results with the renderings to select one or more findings, wherein the diagnostic test results comprise a radiographic image, a magnetic resonance imaging image and a positron emission tomography image.

5. The system of claim 1 further comprising a screen permitting the user to select medical references and differential diagnoses related to the selected anatomical region.

6. The system of claim 1 wherein the patient medical history information comprises one or more of a type of injury, symptoms, a duration of symptoms and symptoms progress.

7. The system of claim 1 wherein the screen requesting selection of an anatomical region of the patient further comprises a screen requesting selection of the anatomical region and conditions associated with the selected anatomical region.

8. The system of claim 1 wherein the screen presenting possible findings comprises a plurality of screens, and wherein each screen of the plurality of screens includes an icon identifying that all examination observations for findings displayed on the screen are normal.

9. The system of claim 1 wherein the system is accessible via a web site.

10. The system of claim 1 wherein the patient medical history information comprises one or more of chief physical complaint, implant data, type of appointment, symptoms duration, type of injury and symptoms progress.

11. The system of claim 1 wherein the patient transcript comprises an ICD-9 code based on a fracture pattern, arthritic changes, hardware implant failures and joint pathology, and wherein the ICD-9 code is automatically generated by the system responsive to user inputs.

12. The system of claim 1 further comprising a screen displaying a warning responsive to an error in entered information or responsive to an omission of information.

13. The system of claim 1 wherein the patient transcript comprises standard nomenclature and is stored in ACCII format.

14. The system of claim 1 wherein the transcript is searchable to study healing of specific fractures, to track medical device implants, to identify patients who may require follow-up evaluation and to search medical records for retrospective studies.

15. The system of claim 1 wherein the anatomical regions comprise spine, upper extremity, hand, wrist, lower extremity, foot, ankle and pelvis.

16. The system of claim 1 associated with a web site, the system further comprising web links to patient implant information and physician educational information, wherein one or more of the web links are to implant manufacturer's web sites.

17. The system of claim 1 further comprising a screen prompting the user to electronically sign the transcript.

18. A computer-implemented method for guiding a user's examination of a patient and for generating a transcript, the method executed by a processor in communication with an output display device and a user interface, the processor programmed to execute steps comprising:

(a) the processor requesting patient identification information and further requesting patient medical history information;

(b) the processor requesting vital signs information;

(c) the processor requesting patient symptoms information from among a plurality of symptoms, wherein a user can identify one or more observed symptoms as selected from among the plurality of symptoms or the user can indicate that no symptoms are observed;

(d) in response to the user identifying one or more observed symptoms, the processor requesting selection of an anatomical region of the patient for examination, wherein the user selects the anatomical region based on one or more of the observed symptoms;

(e) the processor requesting selection of an anatomical subregion within a selected anatomical region, wherein the user selects the anatomical subregion based on one or more of the observed symptoms;

(f) the processor presenting a plurality of screens displaying renderings of the selected anatomical subregion and possible findings associated with a condition of the patient as related to the selected anatomical subregion, each rendering displaying normal and abnormal conditions of the selected anatomical subregion to assist the user with selecting one or more findings, and wherein more-detailed renderings are provided responsive to user control;

(g) the processor presenting additional renderings responsive to user selection of one or more findings; and (h) the processor generating a patient transcript responsive to information entered during the steps (a) through (g) and displaying the patient transcript.

19. The method of claim 18 wherein the patient transcript includes information regarding a selected rendering that best describes a patient's condition, the selected rendering using standard nomenclature.

20. The method of claim 18 wherein the renderings comprise skeletal line drawings, anatomical images and photographs.

21. The method of claim 18 further presenting a screen permitting the user to select medical references and differential diagnoses related to the observed symptoms.

22. The method of claim 18 wherein the step of presenting a plurality of screens further comprises presenting an icon indicating that all examination observations for findings displayed on the output display device are normal.

23. The method of claim 18 wherein the patient transcript comprises an ICD-9 code based on a fracture pattern, arthritic changes, hardware implant failures and joint pathology, and wherein the ICD-9 code is automatically generated responsive to user inputs.

24. The method of claim 18 wherein the patient transcript comprises standard nomenclature and is stored in ASCII format.

25. The method of claim 18 associated with a web site, the method further comprising presenting web links to patient implant information, physician educational information and patient educational information.

26. The method of claim 18 further comprising prompting the user to electronically sign the patient transcript.

\* \* \* \* \*